United States Patent [19]
Samuel et al.

[11] Patent Number: 5,399,314
[45] Date of Patent: Mar. 21, 1995

[54] STERILIZING AND DESORBING EQUIPMENT

[75] Inventors: Alan H. Samuel, Cardiff; Ian P. Matthews, both of Cardiff, United Kingdom

[73] Assignee: The University of Wales College of Medicine, Cardiff, United Kingdom; a part interest

[21] Appl. No.: 28,933

[22] Filed: Mar. 8, 1993

Related U.S. Application Data

[63] Continuation-in-part of Ser. No. 662,325, Feb. 25, 1991, Pat. No. 5,209,902, which is a continuation of Ser. No. 893,544, Jul. 7, 1986, abandoned.

[51] Int. Cl.$^6$ .............................................. A61L 2/14
[52] U.S. Cl. .................................. 422/34; 422/22; 422/30; 422/297; 422/300; 422/305; 422/307; 250/455.11
[58] Field of Search .................... 422/21–22, 422/30, 34, 297, 300, 305, 307; 250/455.1; 55/2, 279

[56] References Cited

U.S. PATENT DOCUMENTS 3,753,651 8/1973 Boucher .................................. 21/54
3,955,286 5/1976 Anrep ........................................ 34/1

FOREIGN PATENT DOCUMENTS

62309/90 12/1990 Australia.

OTHER PUBLICATIONS

By W. Fehse et al., "The Construction of a Microcomputer Controlled Microwave–Microwave Double Resonance Spectrometer Incorporating Two Crossed Fabry–Perot Resonators", 1983, pp. 263–270, vol. 97, The Netherlands.
By W. Kolbe et al., "GHz pulsed Fourier transform microwave spectrometer", Jan. 1985, pp. 97–102, vol. 56, No. 1.
By A. Dymanus, "High-Q Stark Cavity Absorption Cell for Microwave Spectrometers", Mar. 1959, vol. 30, Nov. 3, pp. 191–195.
By L. Hrubesh et al., "A Gunn Diode Microwave Cavity Spectrometer", 1969, pp. 595–560.
By R. Collier, "Variable-Frequency Microwave Cavity Spectrometer", Dec. 1954, vol. 25, No. 12, pp. 1205–1207.
B. W. Kolbe et al., "140 GHz Microwave Spectrometer for the Detection of Gaseous Chemical Species", 1983, pp. 733–749.
By G. Reesor et al., "X-band Spectrometer with a Rectangular Resonant Stark Cell", Jun. 1975, vol. 46, No. 6.
By R. Nandi et al., "Microwave–microwave double resonance using a Fabry–Perot cavity spectrometer", Oct. 1983, vol. 54, No. 10, pp. 1377–1379.
By H. Uehara et al., "Continuous ammonia monitor using a Stark microwave cavity resonator onator", Mar. 1980, vol. 51, No. 3, pp. 334–337.
By M. Lee et al., "A Cavity Type Absorption Cell for Double Resonance Microwave Spectroscopy", Apr. 1972, vol. 43, No. 4, pp. 638–640.
By H. Uehara et al., "A Sensitive Microwave Cavity Spectrometer: Direct Detection of Formaldehyde in Automobile Exhaust", Oct. 15, 1974, vol. 28, No. 4, pp. 597–599.
By L. Hrubesh et al., "A Cavity Search Spectrometer for Free Radical Microwave Rotational Absorption Studies", Jun. 1971, vol. 42, No. 6, pp. 789–796.

*Primary Examiner*—Lyle A. Alexander
*Attorney, Agent, or Firm*—Young & Thompson

[57] ABSTRACT

A steriliser apparatus includes a chamber in which an article or material to be sterilised is placed and a sterilising gas or vapour is then introduced into the chamber to contact and sterilise the article or material. The free sterilant gas or vapour in the chamber is removed and the article or material subjected to a desorbing step during which the concentration of sterilising gas or vapour in the chamber is measured by a sampling device in which a sample of chamber atmosphere is exposed to microwave radiation and the absorption spectrum monitored to determine the concentration of sterilising gas or vapour present in the chamber.

18 Claims, 5 Drawing Sheets

STERILIZING AND DESORBING EQUIPMENT

This application is a continuation-in-part of application Ser. No. 07/662,325, filed Feb. 25, 1991, now U.S. Pat. No. 5,209,902, which is a continuation of Ser. No. 06/893,544, filed Jul. 7, 1986, now abandoned.

FIELD OF THE INVENTION

This invention relates to the sterilizing of articles to kill or destroy bacteria or other unwanted or toxic bodies. The invention is of particular utility in the sterilizing of equipment used for medical or surgical purposes, but may have other applications, for example in industry. This invention also relates to the desorption of gas or vapor from articles or material, and extends in particular to apparatus and methods for measuring the presence or concentration of sterilant, or the gas or vapor to be desorbed in the above sterilizing and desorbing techniques. Such apparatus and methods may be used to control sterilizing and desorbing apparatus and improve their operation.

BACKGROUND OF THE INVENTION

It is of course well known to sterilize metal surgical instruments by steam and it has also been common practice to sterilize various articles in sterilizing liquids. High temperature steam sterilizing is simple and effective for certain metal objects, but has limitations and disadvantages, for example it is inefficient in sterilizing any object which a sealed package, and the high temperatures involved may cause degradation of plastic articles. The use of sterilizing liquids also has limitations, for example air bubbles may be trapped within the object thus preventing full effectiveness, and it may be difficult or impossible to remove all trace of the liquid afterwards.

It has also been common practice to sterilize medical or surgical equipment by means of a toxic gas and many existing sterilizers in hospital use, for example, involve contacting the articles with ethylene oxide in a sealed sterilizing chamber. Ethylene oxide is an extremely effective bactericide, and is effective not only for metal objects such as surgical implements, but also relatively delicate instruments and equipment, including synthetic plastics. The gas is effective at medium or low temperatures and thus the effects of high temperatures on degrading materials can be avoided. The gas penetrates or permeates plastic wrappings and can thus be used to sterilize pre-packaged objects.

Ethylene oxide is, however, extremely toxic to human beings and after its use for sterilizing it is important that steps be taken to remove all traces, as far as possible. To this end it is known to flush out the interior of the sterilizing chamber or autoclave with fresh air after the sterilizing gas has been extracted. It has also been proposed to "pulse" or vary the pressure of the flushing air during the flushing operation.

One of the problems involved is that the ethylene oxide is absorbed into a number of typical plastic materials which may need to be sterilized, and to "desorb" the gas from the plastics appears to be extremely difficult. Even after the sterilizing chamber has been flushed the desorption of the gas from the objects may result in contaminating the atmosphere of the laboratory or other workroom to a concentration of, say, 4 ppm or more which is an unacceptable health hazard.

Ethylene oxide sterilization is normally validated and monitored by biological measurements. This is achieved by demonstrating the killing of standardized preparations or biological indicators of known resistance to ethylene oxide. For routine process monitoring of production cycles after exposure to ethylene oxide, the biological indicators are placed in culture media and incubated to determine growth and survival. However, the incubation and inspection of the indicators typically takes several days and so does not allow real-time monitoring of the efficiency of the sterilization process. Also, whilst indicating whether the sterilizing process has been successful it does not indicate whether the concentration of ethylene oxide is much higher than necessary (i.e. an "overkill") or only just adequate. Nor can it indicate when it is safe to open the sterilizer.

The use of biological monitoring for quality control is less satisfying than parametric monitoring because of the inherent variability of biological monitors and associated recovery restraints.

In Yeung et al. ("On Line Measurement of the Gaseous Concentration and Relative Humidity in a 100% Ethylene Oxide Sterilisation Cycle", J. Parenteral Drug Association, Vol 33, No. 3, pp 117–124) there is proposed a sterilizer with a dual column gas chromatograph analyzer which samples the atmosphere within the chamber every 90 seconds or so and using a carrier or transfer gas, conveys the sample through the columns which are usually packed with an inert porous support material whereby the different gaseous components are separated and detected. However, whilst capable of regularly sampling the sterilizing chamber atmosphere, a gas chromatograph cannot provide proper real-time measurement of the constituents in the sample because the final measurement is dependent on the slow passage of the sample through the columns.

Also, a characteristic and limiting feature of a gas chromatography analyzer is that the columns cannot be sterilized, or more correctly, if the columns were sterilized it would render them useless for the purpose of measurement.

Furthermore, the act of sampling breaches the all-important sterility or barrier boundary after sterile conditions have been achieved, thus compromising the sterilization procedure.

Yeung et al. suggest that, to prevent the carrier gas from contaminating (either chemically or biologically) the sterilizing chamber, the samples are vented to waste rather than returned to the chamber. This inevitably creates a disposal problem and necessarily alters the in-chamber conditions being measured. Furthermore since there is no constant flow path from the sterilizer to the analyzer and back to the sterilizer, this further frustrates any attempt to obtain measurements in real-time.

SUMMARY OF THE INVENTION

It is an object of this invention to provide an improved sterilizer or desorber in which the presence or concentration of a gas or vapor can be detected substantially in real-time, so that the sterilization or desorption process can be automatically controlled on the basis of these measurements.

It is a further object of this invention to provide a sterilizer or desorber having a sampling means for determining the presence and/or concentration of a gas or vapor, which is capable of sterilization.

It is yet a further object of this invention to provide a sterilizer or desorber having a sampling means capable of measuring the presence and/or concentration of a gas or vapor without interrupting the sterile boundary or barrier around the sterilizing or desorbing chamber and without significantly altering the atmosphere within said diameter.

Accordingly, in one aspect this invention provides a sterilizing apparatus comprising:

a single sterilizing chamber having an opening;

a closure means for closing said opening;

gas seal means for effecting a substantially gastight seal between said closure means and said opening;

radiation seal means for effecting a substantially radiation-tight seal between said closure means and said opening;

means for releasing a sterilizing gas or vapor into the sterilizing chamber after said closure is closed to contact and sterilize an article in the chamber;

means for removing the said gas or vapor from said sterilizing chamber when required whilst the chamber is otherwise sealed;

means for propagating high frequency electromagnetic radiation in said chamber to irradiate the sterilized article to desorb sterilizing gas or vapor therefrom in a desorbing step, whereafter said removing means is adapted also to remove the desorbed gas from the sterilizing chamber and means for sampling or receiving a sample of the atmosphere within said chamber, said sampling means including means for exposing said atmosphere sample to microwave radiation, and means responsive to the absorption of microwave radiation by said sample to determine the presence and concentration of gas or vapor in said sample.

By this arrangement, the presence and concentration of ethylene oxide may be measured in real-time, in a mixture which might contain several constituents, e.g. water vapor, vapors given off by the articles being sterilized, and so on. This means that, in contrast to earlier arrangements, the ability of the sampling means to identify and accurately quantify a particular gas or vapor allows the sampling means to form part of an active control loop. This means that it may no longer be necessary to supply an excessive concentration of sterilant to the sterilizer to provide a generous margin of error. Thus the concentrations of sterilizer used may be considerably reduced, with a corresponding reduction of the amount of time necessary to desorb harmful sterilants and a removal or reduction of the disposal problem. It also allows the sterilant to be recycled because an accurate measure of its concentration can be taken.

Furthermore, the sampling means provides a sensing chamber within which the sample is exposed to radiation and this may easily be sterilized as compared to the non-sterilizable column(s) of the gas chromatograph.

Preferably, said sterilizing means include a sensing chamber into which a sample of said chamber atmosphere is introduced, means for propagating microwave radiation in the sensing chamber and means for varying the quantum mechanical molecular rotational frequencies of the analyte, the frequency of the microwave source and the resonant frequency of the sensing chamber such that they are in sympathy and thereby determine the presence and concentration of said gas or vapor in said chamber.

Preferably, there is at least one passage means connecting said sterilizer chamber and said sampling means whereby atmosphere from said sterilizing chamber passes or is caused to pass into said sampling means; the passage may be natural diffusion or there may be means for causing atmosphere from said sterilizing chamber to circulate through said sampling means.

The apparatus may include control means for controlling said gas or vapor release means, said removing means and said propagating means, said control means being responsive to the concentration of said sterilizing gas or vapor, as determined by said sampling means. The apparatus may be operable to control said release means in response to said sampling means to control the amount of gas or vapor released into said chamber, thereby to limit the concentration of said gas or vapor in said chamber. Said control means is preferably operable to monitor the concentration of said gas or vapor in said chamber during said desorption step and to control said propagating means to control the period of irradiation in accordance with the sensed concentration of said gas or vapor. Likewise, said apparatus may include lock means for locking said closure means and said control means may be operable to actuate said lock means and to allow said closure to be opened only when the concentration of said gas or vapor is below a given level, as determined by said sampling means.

In another aspect, the invention provides a sterilizing apparatus including a sterilizing chamber, means for sampling the atmosphere within said sterilizing chamber, said sampling means including means for exposing said atmosphere sample to microwave radiation by said sample to determine the presence and concentration of gas or vapor in said sample.

In a further aspect, the invention provides a desorbing apparatus, including a desorbing chamber, means for sampling the atmosphere within said desorbing chamber, said sampling means including means for exposing said atmosphere sample to microwave radiation and means responsive to the absorption of microwave radiation by said sample to determine the presence and concentration of gas or vapor in said sample.

In a further aspect, the invention provides a method of sterilizing an article or material which comprises monitoring the presence or concentration of a gas or vapor in the sterilizing chamber by exposing a sample of said chamber atmosphere to microwave radiation and determining the presence or concentration of a selected gas or vapor by observing the absorption of said radiation at a frequency or frequencies corresponding to said selected gas or vapor.

In yet another aspect, the invention provides a method of desorbing gas or vapor from an article or material which comprises exposing said article or material to high frequency electromagnetic radiation in a desorbing chamber and monitoring the presence or concentration of a gas or vapor in the desorbing chamber by exposing a sample of said chamber atmosphere to microwave radiation and determining the presence or concentration of a selected gas or vapor by observing the absorption of said radiation at a frequency or frequencies corresponding to said selected gas or vapor.

The sterilizer described herein makes use of our discovery that microwave energy has important and surprising advantages in the sterilizing field. As will be explained more fully it has a valuable effect in aiding the desorption of a gas such as ethylene oxide, and it also has a valuable synergistic effect in the actual sterilizing process when used in conjunction with ethylene oxide. More particularly, the invention is based in part on the discovery that microwave energy exerts a non-thermal as well as a thermal effect upon materials, and the synergistic use of microwave radiation in conjunction with ethylene oxide gas for sterilization is far more effective than use of either agent alone. This is believed to follow from two allied but different reasons.

Non-thermal effects result directly from the interaction of the electromagnetic field with molecules. When polar molecules are subjected to a strong alternating electromagnetic field their tendency to orientate with the applied field causes a degree of molecular disturbance. Thermal effects, on the other hand, are a consequence of "dielectric loss" in which part of the applied field voltage is resolved as Joule heating due to the inability of the molecular dipole to align with the field with absolute fidelity, i.e. the molecular orientations are slightly out of phase with the applied field due to hindered movement. It has been found that microwaves exert a biocidal effect distinct from that of thermal energy, and it is believed that this may result from their effect on metabolic chemistry, possibly by causing alternations in cell membrane permeability, or by altering the pH (acidity) of the cellular environment, or by modifying weak chemical bonds between cellular macro molecules. Importantly also it is believed that a very advantageous non-thermal biocidal effect of microwaves lies in the degree of absorption of microwave energy by key molecules such as deoxyribonucleic acid (DNA). For these reasons it is believed that microwave irradiated microorganisms are less viable and more susceptible to destruction by ethylene oxide gas. A mode of action involving direct effect upon cellular DNA particularly favors the synergistic use with ethylene oxide gas, which also exerts a direct effect upon DNA.

The biocidal efficacy of ethylene oxide is a consequence of its electrophilic and lipophilic nature and the reactivity of the epoxide ring. It combines very readily with nucleophilic centers on nucleic acids and proteins. The mechanism of DNA alkylation by ethylene oxide is principally at the site of the $N_7$-atom of the base guanine leading to $N_7$-(2-hydroxyethyl) guanine. It is believed that the interaction of the applied microwave electric field with the bonding electrons in molecules of ethylene oxide may induce further significant polarization of bonds, thus enhancing the electrophilic reactivity of the molecular.

For sterilization purposes ethylene oxide gas has sometimes been mixed with freon or carbon dioxide in the proportion of for example 12% E.O. and 88% freon or $CO_2$. In performing the present invention it is possible to use the gas to transfer heat from the material to be sterilized by recycling and compressing the gas (as in a conventional refrigeration process). This may permit a much greater input of microwave energy into the materials thereby enhancing the non-thermal effects whilst maintaining materials at an acceptable temperature.

A preferred embodiment provides sterilizing apparatus comprising a chamber having an access opening and a closure therefor, fluid-tight sealing means for the closure, means for introducing a controlled gas into the chamber and for extracting the gas when required, means for generating or radiating very high frequency electromagnetic radiation in or into the chamber, and means to limit or prevent unwanted escape or discharge of the radiated-energy.

Preferably the closure seal is also provided with means to restrict or prevent escape of electromagnetic radiation and the apparatus also preferably includes a movable support for objects to be sterilized within the chamber, and drive means operable from outside the chamber for actuating the support. The drive means may include a drive coupling between the interior and exterior of the chamber, the coupling being arranged to maintain the positive fluid and radiation seals.

According to another preferred feature of the invention the apparatus includes means to locate a sealed container for the gas or liquid within the chamber and means to discharge the fluid from the container within the chamber, the actuating means being operable from outside the chamber without disturbing the gas or radiation seals.

The radiation generated may be a microwave heating system arranged to create or introduce microwave radiation into the chamber through a sealed wall, "transparent" to the microwave radiation, and the generator may also include means for varying the level of radiation.

Preferably the apparatus includes means for varying or controlling the pressure within the chamber, e.g. above or below atmospheric.

Another aspect of the invention consists in a method of sterilizing an article in which the article is placed in a sealed chamber, sterilizing gas is introduced into the chamber and later withdrawn, high frequency electromagnetic radiation is created or introduced into the chamber to cause internal heating of the article and/or any absorbed gas, and hence desorption of the gas, and the article is then withdrawn from the chamber.

The article is conveniently introduced into and withdrawn from the chamber through a closure which includes a fluidtight seal and a radiation seal.

The gas is conveniently ethylene oxide, which is extremely toxic to human beings and preferably the sterilizing gas, or liquid, is initially contained in a sealed capsule or container placed within the chamber, and the gas is released from the container by an actuator operated externally of the chamber.

Conventional thermometers are not effective in a microwave field and according to another preferred feature of the invention the temperature within the chamber, or of the article, is sensed from outside the chamber by an infrared pyrometer or other remote thermal sensor unaffected by the radiation.

The microwave radiation will normally be created in the chamber after the sterilizing gas has been withdrawn so as to encourage desorption of the gas into the surrounding air or other atmosphere. It may, however, in some cases be of advantage to introduce or create the radiation in the chamber while the sterilizing gas is within the chamber and this may assist the sterilizing process.

In any case the article to be sterilized is preferably moved or rotated within the chamber during exposure to the gas and/or the radiation by means of a motivating system actuated externally.

The invention may also be applied as an additional feature to existing sterilizing equipment and procedures. Thus from another aspect the invention also counts in gas desorbing apparatus for use in conjunction with gas sterilizing apparatus, comprising a fluidtight chamber having an access opening and a closure and fluidtight sealing means for the closure, means for introducing a cleansing or flushing gas such as air into the chamber and for extracting the said gas, means for generating or radiating high-frequency electromagnetic radiation in or into the chamber, and means to limit or prevent unwanted escape or discharge of the radiated energy.

Likewise the invention also consists in a method of desorbing gas absorbed into an article for sterilization, in which the article is placed in a sealed desorbing chamber, high-frequency electromagnetic radiation is created in or introduced into the chamber to cause internal heating of the article and/or any absorbed gas, and hence desorption of the gas, and the article is then removed from the chamber.

According to a preferred feature of the invention the apparatus may include automatic or semi-automatic systems for controlling the cycle, comprising one or more sensors for detecting selected parameters of the operating conditions such as chamber pressure, or temperature, radiation level, concentration of gas, and physical state of actuating elements, together with a programmed controller, and automatic control function elements actuated by the controller for performing selected steps in the cycle.

BRIEF DESCRIPTION OF THE DRAWINGS

The invention may be performed in various ways and one specific embodiment will now be described by way of example with reference to the accompanying drawings, in which.

DETAILED DESCRIPTION OF THE INVENTION

Figure 1:
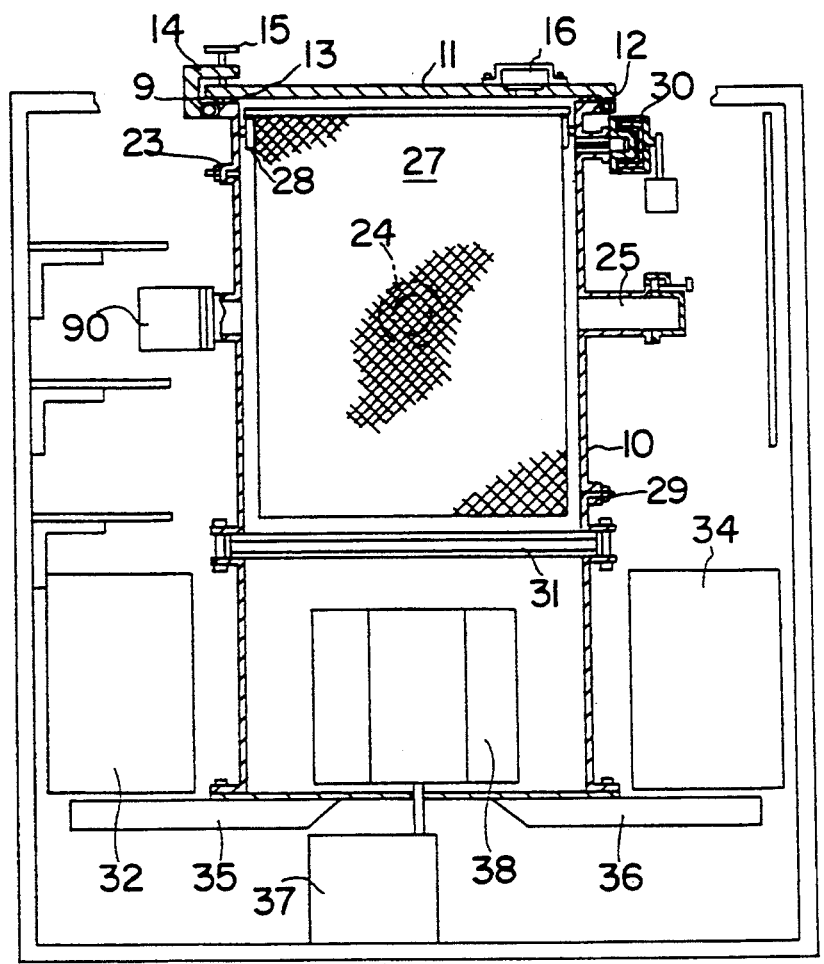
FIG. 1 is a diagrammatic side elevation of a gas sterilizing apparatus according to the invention.
Figure 2:
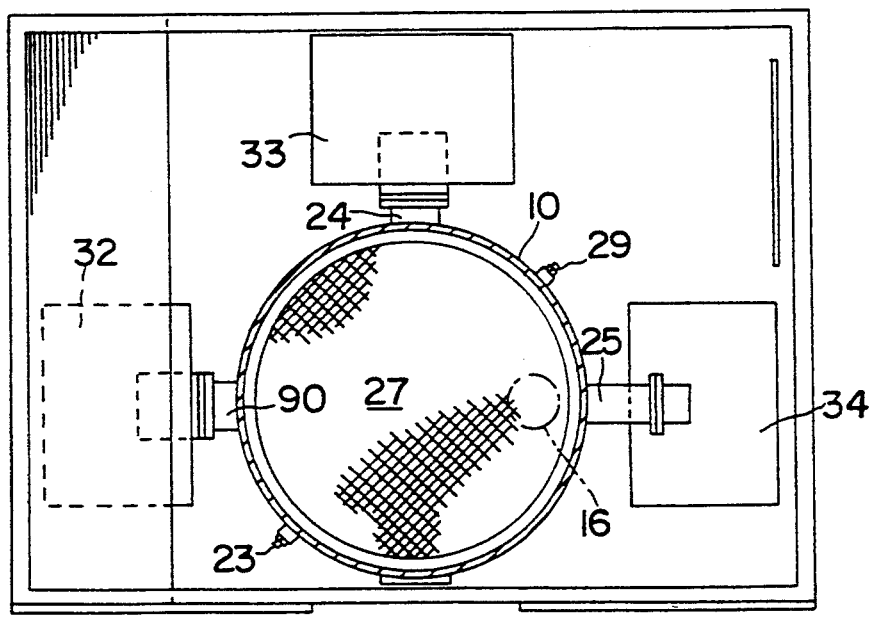
FIG. 2 is a diagrammatic plan view of the apparatus.

Referring first to the essential elements of the apparatus illustrated in FIGS. 1 and 2, the equipment comprises a sterilizing chamber 10 having a stainless steel cylindrical side wall designed to withstand internal pressures, for example of up to five atmospheres, or a partial vacuum. The top of the chamber is closed by a circular lid or cap 11, which is hinged to the side wall at 12 and provided with a circumferential O-ring or other fluid seal 13, and a metallic knit-mesh microwave seal 9. The lid can be held closed by a hinged clamp 14 provided with a tightening screw 15. The lid may also have a rupturable pressure relief disc valve 16, to prevent build up of excessive internal pressures.

On the side of the chamber 10 is an air entry 23 which may be connected to a source of supply for a controlled selected gas, or atmosphere, as required. The side all of the chamber is also provided with another port 29 intended to act as an air outlet, and this may be connected to a special vent duct with a filter, or to atmosphere, as required. The filter conveniently includes a mass of high molecular weight polymeric material designed to adsorb ethylene oxide, from which the gas can later be reclaimed for disposal or recycling. The wall of the chamber is also provided with a microwave spectrometer 24, as illustrated in FIG. 7, and at another part of the side wall is a special sealed injector unit 25 for admitting controlled quantities of ethylene oxide when required. This is illustrated in greater detail in FIGS. 5 and 6.

Figure 3:
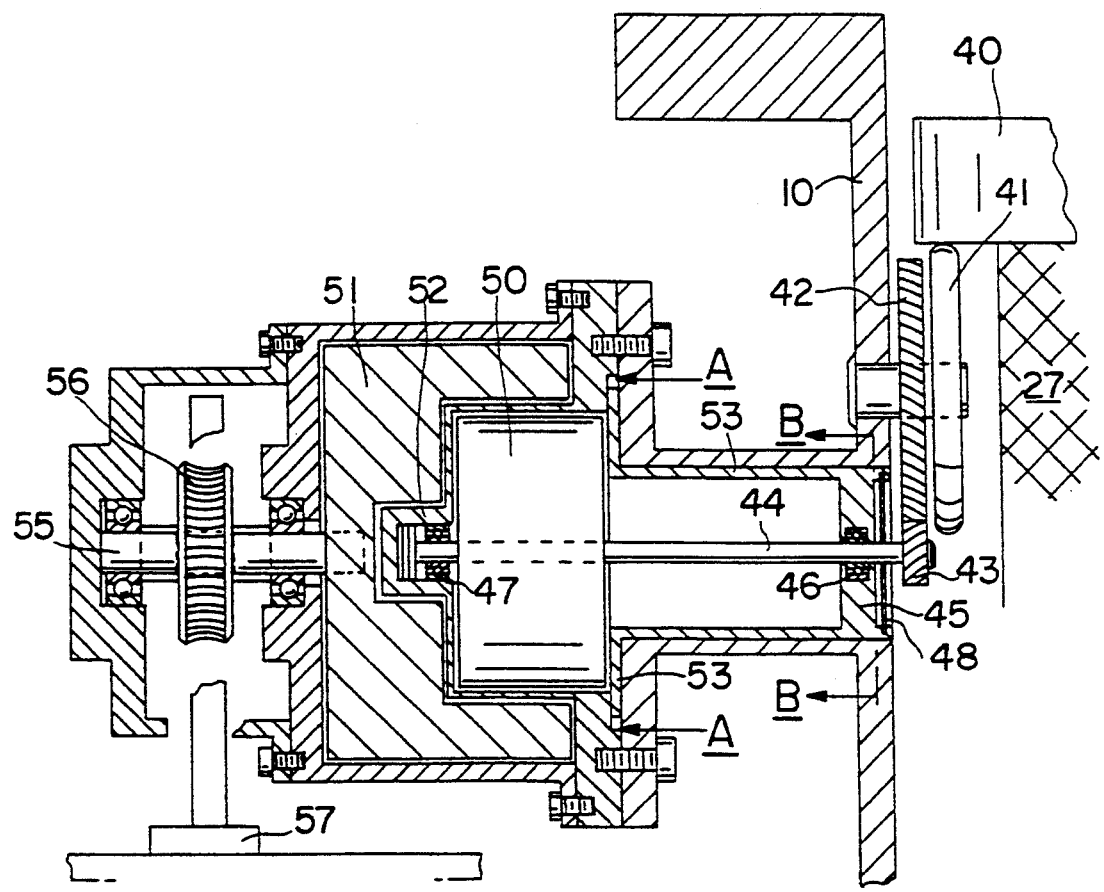
FIG. 3 is a diagrammatic side elevation on an enlarged scale illustrating the drive mechanism and coupling for rotating the internal support basket.
Figure 4:
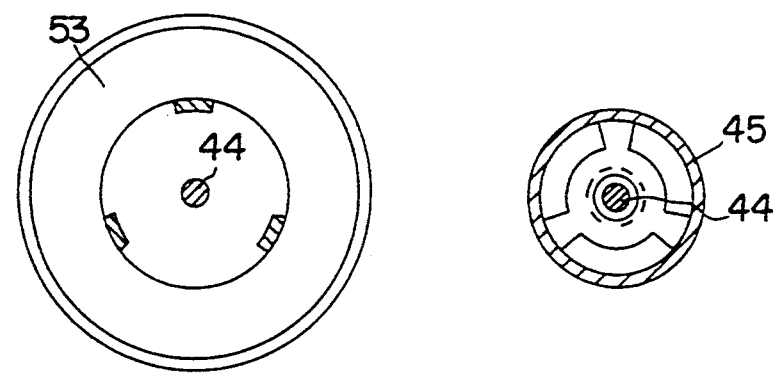
FIG. 4 is a diagrammatic view illustrating two components of the drive coupling.

Within the chamber is a rotary basket 27 for equipment to be sterilized, the basket being supported by bearings 28 mounted on the side wall of a chamber and a special drive system 30 for causing rotation of the basket is illustrated in detail in FIGS. 3 and 4. The bottom wall 31 of the chamber is formed of a material such as polypropylene which is capable of transmitting electromagnetic radiation and acts as a microwave window, and below the chamber are located three microwave generators 32, 33, 34 associated with launching "horns" 35, 36 and a "mode stirrer" 38 driven by a motor 37. Means are provided to vary the output of the generator 33 and to augment this as required by one or both of the generators 32, 34 so as to provide for variation over all three ranges.

The drive mechanism for the basket 27, as illustrated in FIGS. 3 and 4, is arranged to provide for effective drive coupling without disturbing the microwave and fluid seals. As illustrated, the basket 27 has an upper rim 40 which is supported on the free bearing rollers 28 and at one point on a driven roller 41 within the chamber wall 10. This roller 41 is connected to a pinion 42 coupled to a smaller pinion 43 on a shaft 44 which passes through an opening in a metallic mesh microwave screen 48, and through an aperture in the wall 45, and is supported by bearings 46, 47. Also mounted on the shaft 44 is a magnetic driven rotor 50 which is closely associated with a driving magnet 51, but sealed therefrom totally by an intervening wall 52 which acts as a positive fluid seal or enclosure and is in permanent static contact with a cylindrical extension 53 of the chamber wall 10. The magnet 51 is mounted on a driven shaft 55 supported in bearings and secured to a gear 56 forming part of a worm drive coupled to a driving motor 57. FIG. 4 illustrates cross-sections through the coupling unit on the lines A—A and B—B in FIG. 3.

Thus it will be seen that control movements imparted by the motor 57 cause rotation of the magnet 51 and hence of the driven rotor 50 and the basket drive roller 41. In this way the basket with its contents can be moved continuously or in intervals as required for optimum sterilization.

Figure 5:
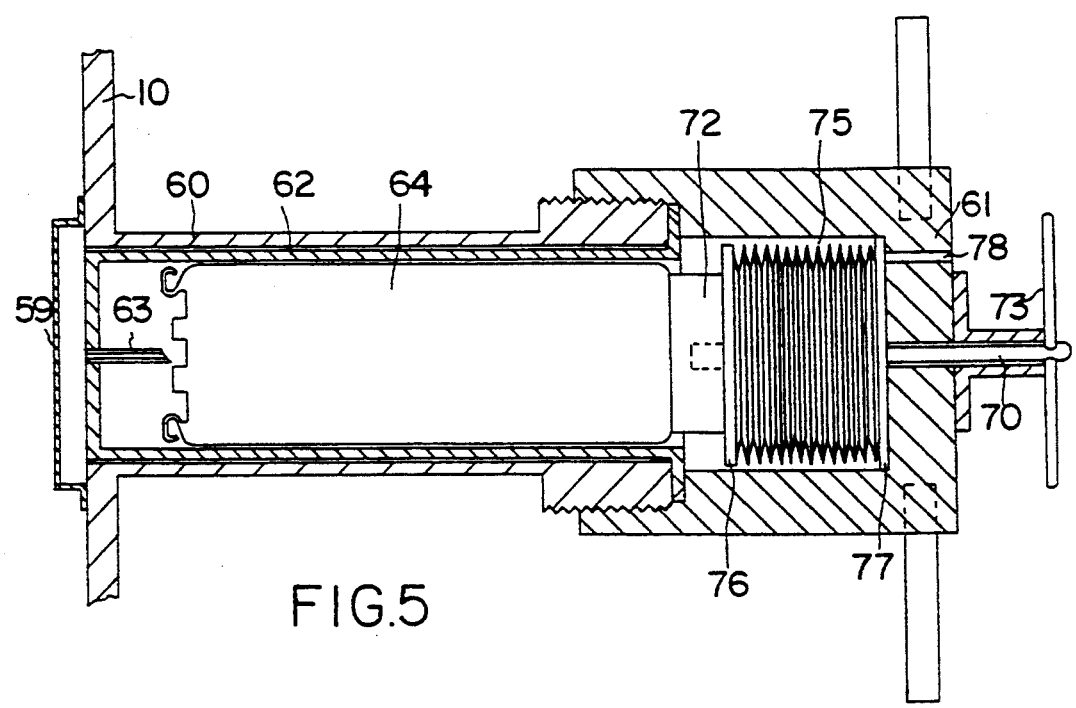
FIG. 5 is a diagrammatic side elevation on an enlarged scale illustrating the sealed internal gas release device.
Figure 6:
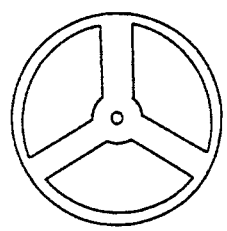
FIG. 6 is a diagrammatic end view illustrating the housing for the capsule puncturing needle.
Figure 7:
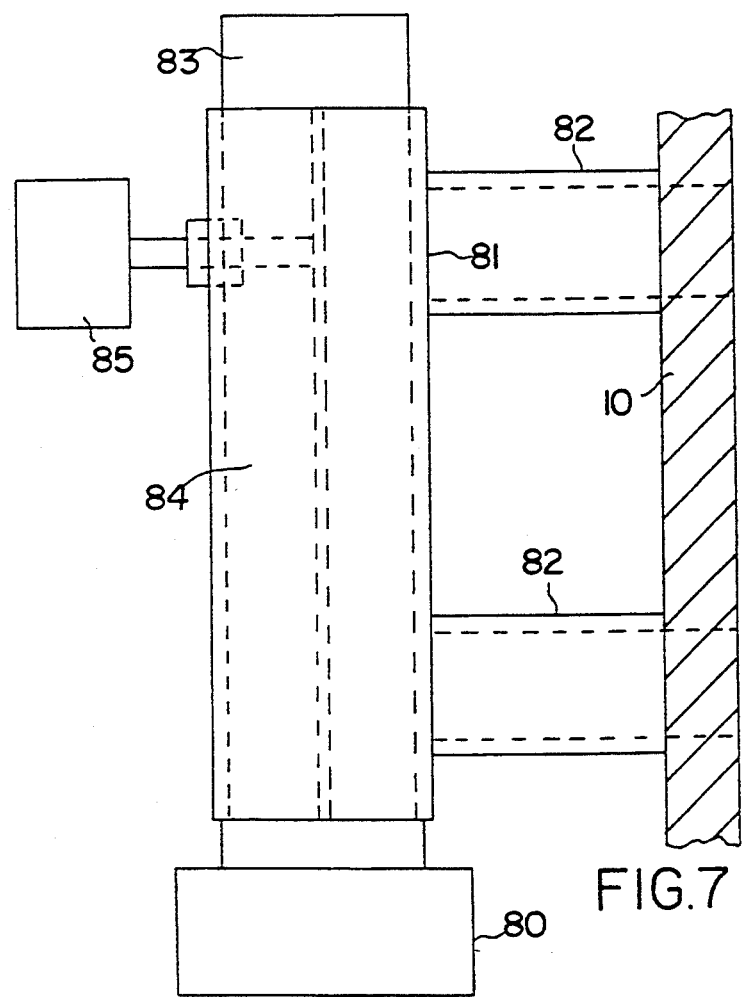
FIG. 7 is a diagram illustrating a microwave spectrometer for detecting ethylene oxide in the equipment.

The ethylene oxide injector illustrated in FIGS. 5 and 6 is arranged to be totally sealed within the chamber 10 but can be actuated externally. The wall 10 of the chamber has an extension 60 to which is positively attached in a fluidtight manner a cylindrical housing 61 and between the two is located a sleeve 62 having a sharp pointed hollow needle 63 at its inner end arranged when required to perforate a sealed capsule 64 containing liquid ethylene oxide. When punctured the liquid contents pass through the needle, impinge upon a baffle plate 59, and are rapidly vaporized into the interior of the chamber. The capsule is forced against the needle by means of an abutment plate 72 which is urged towards the outer end of the capsule by a metal bellow 75 expanded by the pressure of atmospheric air entering the internal void of the bellows via a port 78. The injector unit is permanently sealed off from the atmosphere by the bellows which is closed at its inner end and positively sealed at its outer end to an annulus 77 secured within the cylindrical housing 61. The abutment 72 is provided with a shaft 70 which passes through the void within the bellows and thence through the annulus and the end of the housing 61. The shaft is provided with a manual locking lever 73 which can be pulled outwards and rotated to lock the shaft thus holding the bellows in the contracted position. Evacuation of the main chamber causes the bellows to experience a pressure equal to the difference between atmospheric pressure and chamber pressure. When the shaft is released the pressure differential causes air to enter the internal void of the bellows via the port 78 extending the bellows and driving the abutment plate inwards. For safety reasons this arrangement provides a mean of puncturing the ethylene oxide canisters which will only operate when the chamber pressure is reduced below atmospheric pressure.

FIG. 7 illustrates a microwave molecular rotational spectrometer attached to the chamber 10 for detecting the presence and concentration level of ethylene oxide and other gases. Molecular rotational microwave spectrometry is a fundamental analytical technique. Operating on the principle of quantized absorption of electromagnetic radiation, a molecular dipole in the gas phase will exhibit promotion of its rotational state to one of many available energy levels resulting in a highly characteristic narrow bandwidth (absorption) spectrum unique to that molecular species; reflecting as it does properties of the entire molecule rather than those of just the nucleus or constituent atoms or groups. Furthermore the magnitude of absorption maxima at resonant frequencies is related to the molecular concentration of the analyte and at low pressures when molecular interactions are at a minimum a linear concentration relationship is established. Absorption "peaks" for many compounds may be detected at frequencies between 10 Gigahertz and 40 Gigahertz. The spectrometer illustrated in FIG. 7 is comprised of a rectangular wave guide tube 81 defining a sensing chamber 84 and having a Klystron, Gunn diode or other suitable low power monochromatic microwave generator 80 at the lower end and a microwave detector 83 at the upper end. The interior of the tube is connected to and communicates with the interior of the main chamber 10 via two rigid welded branch tubes 82 each equipped with a microwave choke to prevent the escape of microwave energy while permitting the free diffusion of gases and vapors via suitable permeable septa. Within the tube 81 is a thin insulated metal strip electrode positioned centrally along the major axis of the tube. This electrode is connected to an external alternating square wave voltage source 85 such that a potential difference arises between the electrode and the tube during every half of the alternating voltage cycle giving rise to "Stark" splitting of the angular momentum of the molecular dipoles and a corresponding shift in the frequency of the microwave absorption for the particular molecular rotational transition under observation. The microwave detector passes signals to a detector amplifier which incorporates a phase sensitive discriminator operating synchronously with the "Stark" modulated voltage. The detector amplifier output thus reflects microwave energy absorption occurring each half cycle during zero electrode-potential. This arrangement improves sensitivity by improving the signal to noise ratio. According to another preferred feature where greater spectrometer sensitivity is required the waveguide tube 81 may be replaced by a microwave resonant cavity of high quality (Q) factor connected to and communicating with the interior of the main chamber as previously described and having a monochromatic microwave generator and a microwave detector at appropriate positions and a central electrode with which to employ the "Stark" effect.

The pressure of the gas sample in the spectrometer is approximately 20 millitorr maintained by a high vacuum pump. Gas molecules diffuse into the spectrometer through permeable septa.

Figure 8:
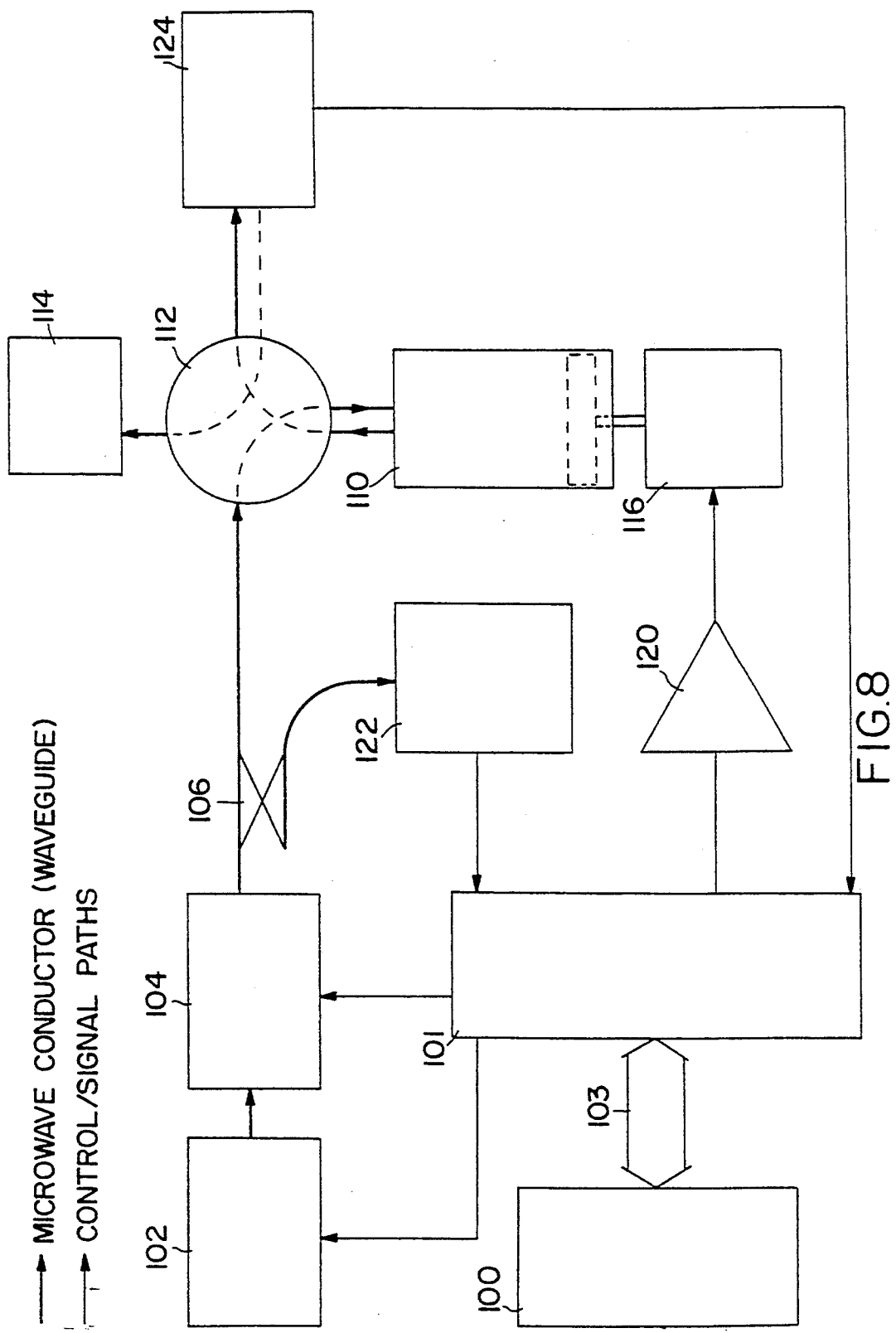
FIG. 8 is a diagram illustrating components of a microwave spectrometer system for use in performing the invention.

According to yet another preferred feature a microwave rotational spectrometer utilizing multiple sequential scanning as a means of signal enhancement which obviates the need for Stark modulation voltages may be used. FIG. 8 is a schematic diagram of such a spectrometer control system for use in controlling the process of ethylene oxide sterilization. In this system a microprocessor unit 100 is arranged to control automatically the operation of the instrument and analyze the data received from the power measuring devices. An interfacing unit 101 includes electronic circuitry to link the microprocessor data bus 103 to the remainder of the spectrometer components. A Gunn diode oscillator 102, under the control of the microprocessor is arranged to "search" for a specific absorption peak by sweeping a preselected frequency band. The power output from the oscillator is limited by means of a precision attenuator 104. A directive coupling 106 splits the microwave beam from the Gunn oscillator into two halves so that the power incident upon the gas filled cavity 110 may be continuously monitored by sensing one half of the beam. A waveguide circulator 112 enables the other half of the microwave beam to be fed into/out of the same cavity orifice. This avoids the possibility of interference between the incident and transmitted beams which would adversely affect the accuracy of measurement. A power absorbing load 114 soaks up any microwave power reflected from the measuring devices.

The tunable resonant cavity 110 has its resonant frequency varied electromechanically in order to match it to the frequency of the input radiation. As a result, at resonance the microwave beam will pass through the comparatively small volume of gas very many times, thus greatly increasing the efficiency of the absorption.

The necessary minute changes in cavity geometry are achieved with the desired degree of precision by means of a piezoelectric positioning device 116. This converts changes in an applied voltage into changes in mechanical displacement (up to 100 microns). The device 116 is powered by an amplifier 120 controlled from the microprocessor interfacing unit 101, and there are two power measuring devices 122, 124 also associated with the interfacing.

The equipment also includes an infrared remote pyrometer, illustrated diagrammatically at 90, on the side wall of the chamber 10, which enables temperature readings to be obtained within the chamber without affecting or being affected by the microwave field.

The equipment may also include an internal pressure sensor designed to avoid interference with the microwave field and arranged not to affect the positive sealing of the chamber.

Figure 9:
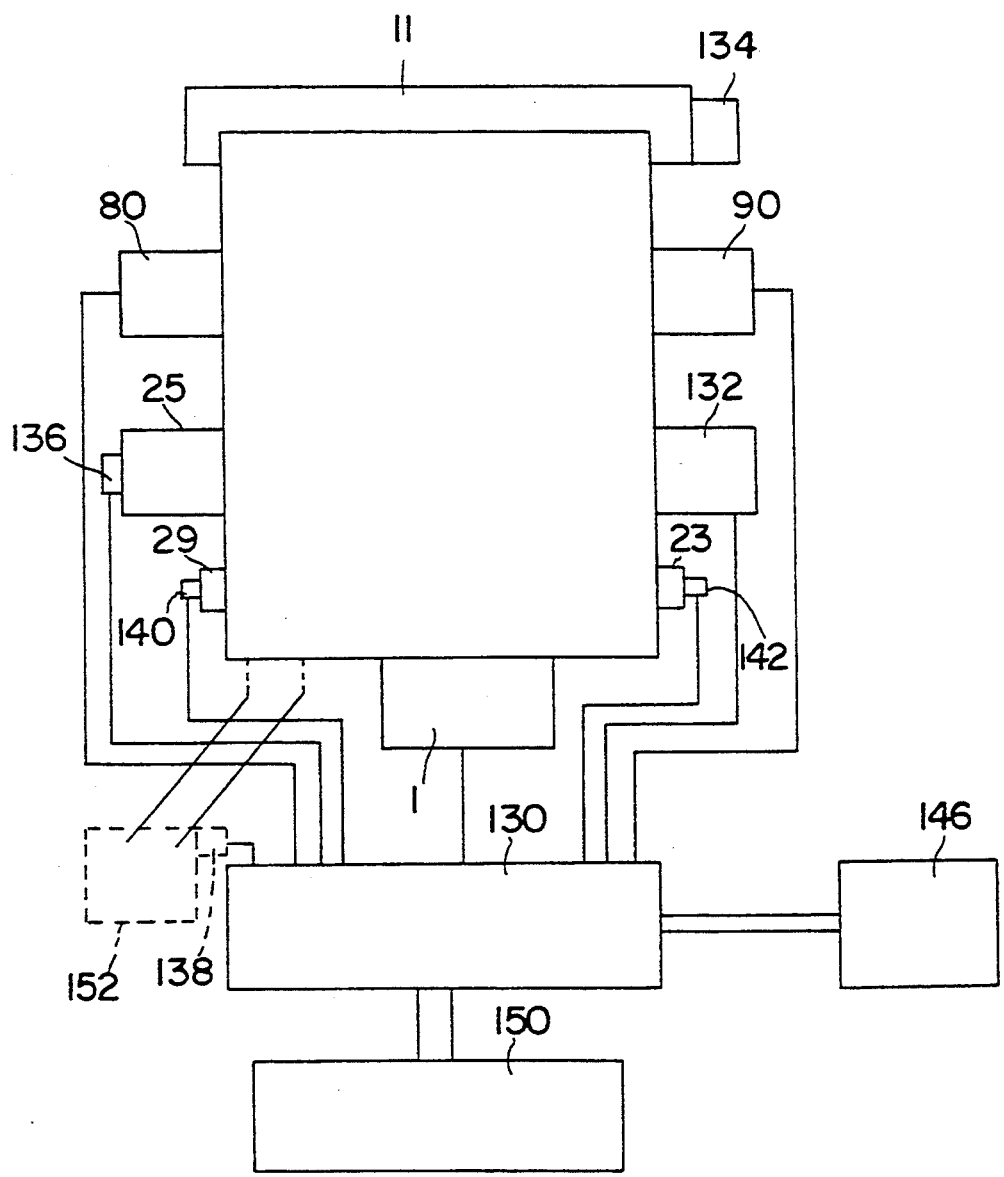
FIG. 9 is a diagram illustrating a general automatic control system for a sterilizing/desorbing cycle.

The whole equipment is conveniently controlled by an automatic or semi-automatic control system, as illustrated diagrammatically in FIG. 9. One possible layout includes a central microprocessor unit 130 having a number of inputs from sensors associated with the equipment, and output functions which may be fully automatic or may be in the form of indicators for use by an operator. Amongst other possible sensors forming part of the control is the spectrometer 80–85, as illustrated in FIG. 7, and in addition the infrared pyrometer 90, or other temperature sensor, a vacuum gauge or pressure sensor 132 for the interior of the chamber, and a number of safety microswitches, for example switch 134, to indicate that the cover 11 is safely closed and fluidtight, switch 136 to show that the ethylene oxide injector 25 is also closed, switch 138 to show that the vacuum pump is or is not operating, and switches 140, 142 to show that the air vent 29 or the air inlet 23 is open or closed. In addition, there is a multiple function timer 146 providing both a fractional time count for individual steps in the process and an overall time measurement. The microprocessor outputs provide control of solenoid operated valves and other control functions via an interface 150. These automatically controlled function elements include valves or actuators associated with the ethylene oxide injector 25, the air inlet and vent 23, 29, the vacuum pump 152, and the microwave generators 32, 33, 34.

The preferred "duty cycle" for the equipment is as follows:

(a) Pre-treatment of the objects to be sterilized including partial evacuation of air from the chamber combined with a humidifying step by addition of water vapor to ensure that bacteria spores and vegetative forms are more susceptible to ethylene oxide. This may be followed by a flushing out of the chamber with other gases, for example $CO_2$.

(b) The Sterilizing Stage

Ethylene oxide is admitted under subatmospheric partial vacuum conditions and sterilization continues either for a fixed time or until predetermined parameters are reached as determined by the sensors on the equipment. During this sterilization the internal pressure in the chamber returns nearly to atmospheric as a result of the injection of ethylene oxide.

(c) Flushing

The ethylene oxide is pumped out of the chamber and the pressure reduced to a substantial vacuum. Flushing air is then admitted and the chamber again evacuated and pumped down to a lower vacuum. This pulsing may continue through several cycles.

(d) With the chamber pressure at some predetermined pressure below atmospheric the microwave generator is actuated and allowed to run for a period of time, which may be set by an automatic timer or determined by readings obtained from the sensors particularly the microwave spectrometer which gives an indication of the ethylene oxide remnant in the chamber. At the end of the microwave stage the chamber is again pumped out and there may be a further flushing step with clean air. Provided that the parameters are then within the specified ranges, particularly the reading of the spectrometer, the cycle terminates and the cover is automatically unlocked.

The arrangement described above provides a sterilizer or a desorber with a sensor which detects the presence and/or concentration of a gas or vapor and which can itself be sterilized. Furthermore, the sensor can be operated with its measuring cell as an integral part of the sterilizer chamber without any non-sterilizable interface intervening, thus assuring preservation of sterile conditions during the sterilization process.

Also, microwave rotational spectrometry as used here provides a primary measurement (i.e. one dependent on a fundamental constant of the analyte specimen) and does not need to be related to a secondary standard, as for example is required in gas chromatography.

This technique of quantitative measurement of gases by microwave rotational spectrometry relies on the fact that the molecular system will absorb energy at some very sharply defined frequencies across the microwave spectrum. Thus this technique relies solely upon the intervention of microwave radiation with the molecular species of interest and consequently yields a primary measurement of the number of molecules of the species of interest. The technique allows the unequivocal measurement of a particular gas or vapor in a complex mixture of unknown compounds and also the ability to identify and quantify the appearance of unexpected spectral features in relation possibly to "alien" analyte species.

The specificity of the technique is very high and the probability of overlap between lines of different species even in gas mixtures of very many component gases is very low. The quantitative analysis by microwave spectrometry does not require the use of standards and furthermore allows measurements to be taken over a wide dynamic range ($1°$ to $10°$ ppm).

We claim:

1. A sterilizing apparatus comprising:
a single sterilizing chamber having an opening;
a closure means for closing said opening;
gas seal means for effecting a substantially gastight seal between said closure means and said opening;
radiation seal means for effecting a substantially radiation-tight seal between said closure means and said opening;
means for releasing a sterilizing gas or vapor into the sterilizing chamber after said closure is closed to contact and sterilize an article in the chamber;
means for removing the said gas or vapor from said sterilizing chamber when required whilst the chamber is otherwise sealed;
means for propagating high frequency electromagnetic radiation in said chamber to irradiate the sterilized article to desorb sterilizing gas or vapor therefrom in a desorption step, whereafter said removing means is adapted also to remove the desorbed gas from the sterilizing chamber;
means for sampling or receiving a sample of the atmosphere within said chamber, said sampling means including means for exposing said atmosphere sample to microwave radiation and means responsive to the absorption of microwave radiation by said sample to determine the presence and concentration of gas or vapor in said sample; and
control means for controlling said gas or vapor releasing means, said removing means and said propagating means; said control means being responsive to the concentration of said sterilizing gas or vapor, as determined by said sampling means.

2. Sterilizing apparatus according to claim 1, wherein said sampling means includes a sensing chamber into which a sample of said chamber atmosphere is introduced, means for propagating microwave radiation in the sensing chamber and means for varying the quantum mechanical molecular rotational frequencies of the sample, the frequency of the microwave source and the resonant frequency of the sensing chamber such that they are in sympathy and thereby determine the presence and concentration of said gas or vapor in said sterilizing chamber.

3. A sterilizing apparatus according to claim 1, including lock means for locking said closure means and wherein said control means is operable to actuate said lock means and to allow said closure to be opened only when the concentration of said gas or vapor is below a given level, as determined by said sampling means.

4. A sterilizing apparatus according to claim 1, including passage means connecting said sterilizing chamber and said sampling means whereby atmosphere from said sterilizing chamber passes or is caused to pass into said sampling means.

5. A sterilizing apparatus according to claim 4, including means for causing atmosphere from said sterilizing chamber to circulate through said sampling means.

6. A sterilizing apparatus according to claim 1, wherein said control means is operable to control said releasing means in response to said sampling means to control the amount of gas or vapor released into said chamber, thereby to limit the concentration of said gas or vapor in said chamber.

7. A sterilizing apparatus according to claim 6, wherein said control means is operable to monitor the concentration of said gas or vapor in said chamber during said desorption step and to control said propagating means to control the period of irradiation in accordance with the sensed concentration of said gas or vapor.

8. A sterilizing apparatus including a sterilizing chamber, means for releasing a sterilizing gas or vapor in said sterilizing chamber, means for sampling the atmosphere within said sterilizing chamber, said sampling means including means for exposing the atmosphere sample to microwave radiation and means responsive to the absorption of microwave radiation by said sample to determine the presence and concentration of gas or vapor in said sample, and means for removing said sterilizing gas or vapor from said sterilizing chamber, control means responsive to the concentration of said sterilizing gas or vapor as determined by said sampling means, to control said releasing means and said removing means.

9. A sterilizing apparatus according to claim 8, wherein said control means is operable to control said release means in response to said sampling means to control the amount of gas or vapor released into said chamber to thereby limit the concentration thereof.

10. A sterilizing apparatus according to claim 8, wherein said control means is operable to prevent access to said sterilizing chamber until the concentration of sterilizing gas or vapor is below a given level.

11. A sterilizing apparatus according to claim 8, wherein said sampling means includes a sensing chamber into which said atmosphere sample is introduced, means for propagating microwave radiation in the sensing chamber and means for varying the quantum mechanical molecular rotational frequencies of the sample, the frequency of the microwave source and the resonant frequency of the sensing chamber such that they are in sympathy and thereby determine the presence and concentration of gas or vapor in said sterilizing chamber.

12. A sterilizing apparatus according to claim 11, including passage means connecting said sterilizing chamber and said sampling means whereby atmosphere from said sterilizing chamber passes or is caused to pass into said sampling means.

13. A sterilizing apparatus according to claim 12, including means for causing atmosphere from said sterilizing chamber to circulate through said sampling means.

14. A desorbing apparatus, including a desorbing chamber, means for propagating radiation in said desorbing chamber thereby to desorb gas or vapor from articles or materials therein, means for sampling the atmosphere within said desorbing chamber, said sampling means including means for exposing the atmosphere sample to microwave radiation and means responsive to the absorption of microwave radiation by said sample to determine the presence and concentration of gas or vapor in said sample, and means for removing gas or vapor from said desorbing chamber, and control means responsive to the concentration of said gas or vapor as determined by said sampling means, to control said propagating means and said removing means.

15. A desorber apparatus according to claim 14, wherein said sampling means includes a sensing chamber into which said atmosphere sample is introduced, means for propagating microwave radiation in the sensing chamber and means for varying the quantum mechanical molecular rotational frequencies of the sample, the frequency of the microwave source and the resonant frequency of the sensing chamber such that they are in sympathy and thereby determine the presence and concentration of gas or vapor in said desorbing chamber.

16. A desorbing apparatus according to claim 15, wherein said control means is operable to cause said propagating means to operate for a period until the concentration of said gas or vapor as determined by said sampling means is below a given level.

17. A desorber apparatus according to claim 14, including passage means connecting said desorbing chamber and said sampling means whereby atmosphere from said desorbing chamber passes or is caused to pass into said sampling means.

18. A desorber apparatus according to claim 17, including means for causing atmosphere from said desorbing chamber to circulate through said sampling means.

* * * * *